United States Patent [19]
Werge et al.

[11] Patent Number: 5,465,938
[45] Date of Patent: Nov. 14, 1995

[54] UNIVERSAL FLUID FLOW CONTROL

[76] Inventors: Robert W. Werge, 60 Ballouville Rd., Dayville, Conn. 06241; Peter N. Kotsifas, 7 Lakewood Trail, Sturbridge, Mass. 01518

[21] Appl. No.: 25,021

[22] Filed: Mar. 2, 1993

Related U.S. Application Data

[63] Continuation-in-part of Ser. No. 804,811, Dec. 9, 1991, Pat. No. 5,190,067, which is a continuation-in-part of Ser. No. 530,097, May 29, 1990, Pat. No. 5,070,905.

[51] Int. Cl.$^6$ ................................................. F16K 15/14
[52] U.S. Cl. .................................... 251/149.1; 137/843
[58] Field of Search ........................ 251/149.1; 137/843, 137/903

[56] References Cited

U.S. PATENT DOCUMENTS

| | | | |
|---|---|---|---|
| 3,385,301 | 5/1968 | Harautuneian | 137/843 X |
| 4,681,132 | 7/1987 | Lardner | 137/843 X |
| 4,683,916 | 8/1987 | Raines | 251/149.1 X |

*Primary Examiner*—Robert G. Nilson
*Attorney, Agent, or Firm*—Stephen Y. Chow; Jerry Cohen; Edwin H. Paul

[57] ABSTRACT

A flow control device in which a flow channel includes a flow control member in the form of a domed disk with legs by which the disk is seated to seal the channel. The control member can be acted upon by an internal actuator or plunger that extends into the flow channel where the plunger can be engaged by an external member such as a Luer fitting. The actuator or plunger may be of rigid or flexible construction.

11 Claims, 13 Drawing Sheets

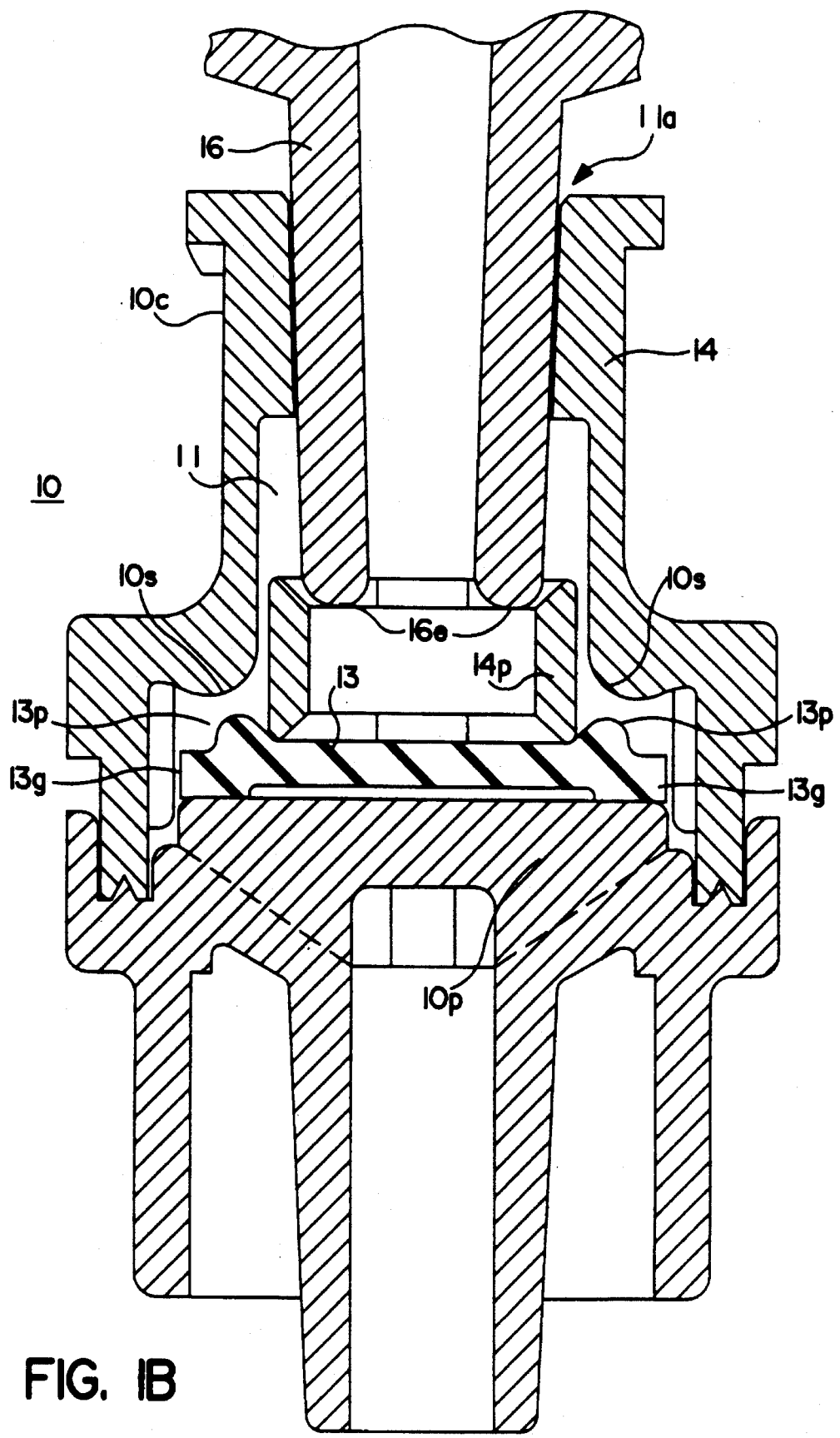
FIG. IB

UNIVERSAL FLUID FLOW CONTROL

This is a continuation-in-part of application Ser. No. 804,811, filed Dec. 9, 1991, and issued as U.S. Pat. No. 5,190,067, Mar. 2, 1993, which in turn was a continuation-in-part of Ser. No. 07/530,097, filed May 29, 1990, and issued as U.S. Pat. No. 5,070,905, Dec. 10, 1991.

BACKGROUND OF THE INVENTION

The invention relates to flow control and more particularly, to the universal control of fluid flow and injected fluids in valves by devices such as Luer fittings, plastic cannulas and needles, both blunt and sharp.

It often is desirable to control the flow of fluids such as liquids and gases. A common device for that purpose is a valve. The valve functions by the deflection of an elastomeric element towards and away from a valve seat. The deflection is towards the valve seat in order to prevent flow, and away from the seat to permit flow.

In some cases the control of fluid flow is with respect to a multiplicity of channels that have varying degrees of convergence with one another. A typical multiplicating arrangement makes use of connectors which permit the intercalation of flow channels as desired.

An illustrative prior art valve that controls flow is set forth in U.S. Pat. No. 4,610,276 ("'276") which issued Sep. 9, 1986. This patent discloses a flow control valve with a main channel for the through-flow of fluid and a branch channel connected to the main channel at an intermediate position. The valve includes a diaphragm for controlling the flow. The diaphragm is clamped and bowed under pressure into the inlet channel. The application of pressure to the diaphragm assures the sealing of the channel.

While the diaphragm of the '276 patent operates properly in most cases, there is the possibility that the diaphragm will fail to seat properly.

Another valve arrangement is disclosed in U.S. Pat. No. 4,874,369 which issued Oct. 17, 1989. This arrangement employs a duck-bill valve in a configuration that is complex, costly and difficult to manufacture. In addition, duck-bill valves of the type contemplated by the '369 patent have proved to be unreliable in practice, with such difficulties as failure to seal properly.

Other arrangements which relate to the control of fluid flow are disclosed in Osborne U.S. Pat. No. 2,270,468; Goott et al U.S. Pat. No. 3,370,305; Craft U.S. Pat. No. 3,457,933; Rosenberg U.S. Pat. Nos. 3,572,375, 3,650,093 and 3,710,942; Bobo U.S. Pat. No. 3,886,937; Melnick U.S. Pat. No. 3,891,000; Mittleman U.S. Pat. Nos. 4,000,740 and 4,405,316; Stevens U.S. Pat. No. 4,000,739; Zedes et al U.S. Pat. No. 4,005,710; Mittleman et al U.S. Pat. Nos. 4,048,996 and 4,133,441; Rushkie et al U.S. Pat. No. 4,222,407; Sheehan et al U.S. Pat. No. 4,294,249; Spademan U.S. Pat. No. 4,338,934; Paradis U.S. Pat. No. 4,415,003; Spector et al U.S. Pat. No. 4,424,833; Edwards et al U.S. Pat. No. 4,566,493; Goodell U.S. Pat. No. 4,596,265; Suzuki et al U.S. Pat. No. 4,610,674 and Holtermann et al 4,958,661; EPO 0109903; France 2004771 and UK 2033230. None of these arrangements provide the advantages of the invention.

In addition, all of the foregoing valves require the presence of fluid pressure in order to operate the diaphragm, either by exerting pressure to open the diaphragm or by using reverse pressure to close the diaphragm. In some cases it is desirable to be able to act upon the diaphragm by using other than fluid pressure. Thus, a user may want to actuate the diaphragm independently of the presence of fluid pressure, in preparation for anticipated fluid flow. In other cases, it is desirable to maintain a diaphragm in its open position for a prescribed interval of time independently of whether fluid flow is present.

Another consideration that applies in the use of flow control devices is that the fittings used with the devices vary in tolerances. As a result, flow control valves are employed with a variety of fittings. A flow control valve that is suitable for a particular fitting may not function in the same way with a different fitting, even if the fitting is of the same general type, because of tolerance variations.

A further consideration is the need for multipurpose valves which can be used with syringes, such as those with Luer fittings, plastic cannulas and steel needles, whether blunt or sharp.

Accordingly, it is an object of the invention to enhance the control that can be achieved over fluid flow. Another object is to provide a facility for acting upon the diaphragm by using other than fluid pressure. A related object is to permit a user to actuate the diaphragm independently of the presence of fluid pressure, in preparation for anticipated fluid flow.

Still another object is to maintain a diaphragm in its open position for a prescribed interval of time independently of whether fluid flow is present.

A further object is to facilitate the use of flow control devices with fittings that vary in tolerance. A related object is to employ flow control valves with a variety of fittings. Still another related object is to permit a flow control valve that is suitable for a particular fitting to function in the same way with a different fitting, even if the fitting is of the same general type, because of tolerance variations.

A still further object is to achieve greater reliability over valve operation than is achievable by clamped diaphragms and duck-bill valves.

Yet another object is to achieve precision control at reduced cost and simplification.

SUMMARY OF THE INVENTION

In accomplishing the foregoing and related objects the invention provides a flow control device with a channel for the flow of fluid and a domed member seated in the channel for controlling flow therethrough. The device can further include a member for permitting the activation of the controlling mechanism by a member external to the flow control device by engaging the controlling mechanism and depressing the domed member. The domed controlling member can be a cupped disk with a lateral extension by which the disk is seated in the channel.

In accordance with one aspect of the invention, the disk has opposed sides, of which one side is joined to a wall extending in the axial direction of the flow channel, and the other side is movable in the same direction away from its seat under pressure. The seat can have an apex and an annular surface extending on opposite sides of the apex, with the disk positioned against the annular surface and displaceable away from the surface.

In accordance with another aspect of the invention a buttress having opposite ends extends across the channel and the disk is positioned on the ends of the buttress and moved in the axial direction of the channel into contact with the annular surface.

The disk can be a cup having a dome positioned against a seat and legs which extend away from the seat. The cup can have a continuous and circular side wall, as well as a base and legs that extend from the base.

In a method of controlling fluid flow in a channel which is sealed by a flexible member having a sealing surface and an extension therefrom, the steps include (1) compressing the extension from the flexible member to unseal the channel; and (2) allowing fluid to flow in the channel. In the method for controlling the flow of fluid where the flexible member is a domed disk, the step of controlling flow in the channel can be by applying peripheral pressure to the domed disk opposite the extension by which the disk seals the channel. The channel can include a plunger and peripheral pressure is applied by the movement of the plunger against the periphery of the disk. The channel can be adapted to accommodate a Luer fitting and the movement of the plunger can respond to the insertion of a Luer fitting into the channel.

In a method of fabricating a flow control device, the steps include (a) molding a first member of the flow control device, including a seat for the periphery of a control member for sealing a flow channel of the device; (b) molding a second member of the flow control device, including a support at the periphery of the flow channel; (c) inserting the control member on the seat of the first member; and (d) joining the second member to the first member with the peripheral support peripherally compressing the control member against the seat.

A flow control device in accordance with the invention also includes a channel for the flow of fluid; controlling the flow by a disk which is compressed with a circular depression against a ring seat and contactable with a plunger that can unseal the disk. When the channel has a central axis, the disk can be under pressure by a transverse member positioned across the central axis. The disk can be compressed by a radially extending buttress, thereby to limit the extent to which pressure exerted against the disk can force the disk into the channel; and the buttress extends across the circumference of the channel and the interval at each edge of the buttress is tapered to limit the extent to which a gaseous fluid can become entrapped.

The channel can be terminated in a housing containing a domed disk having legs extending laterally therefrom into engagement with means for applying pressure to the disk. The control over the flow of fluid can include the steps of (a) providing a channel for the flow of fluid; (b) controlling the flow in the channel by a sealing member which is restricted from being sucked into the channel. A flow control device in accordance with the invention includes (a) a channel for the control of fluid; (b) a ring seat within said channel; (c) a flexible plunger within said first channel; and (d) a control disk in surface contact with the ring seat and plunger.

In accordance with a further aspect of the invention, the domed member includes slit in its central portion for accommodating a cannula, or similar device. The slit can be surrounded by a depression in the outer surface of the domed member to guide the cannula into the slit and serve as a reservoir for fluid. In addition the slit can be surrounded by a post extending from an inner surface of the domed member to prevent the cannula from depressing the domed member.

In accordance with a method of the invention wherein a domed disk has a central slit therein, a flow channel remains sealed and a cannula is insertable through the slit to allow fluid to flow in the channel. The domed disk can be exposable for sterilization before the cannula is inserted through the slit. The device of the invention can be in two parts, of which the first member is separatable into two subordinate parts in order to expose the control member for direct sterilization.

In accordance with still another aspect of the invention a flow control device can include a channel for the flow of fluid, with a flow control disk which is compressed with a circular depression against a ring seat and contactable with a plunger that can unseal the disk and provided with direct access to permit sterilization.

DESCRIPTION OF THE DRAWINGS

Other aspects of the invention will become apparent after considering several illustrative embodiments, taken in conjunction with the drawings, in which:

FIG. 1B is a further view of FIG. 1A illustrating the action of an internal plunger against the sealing mechanism of the device in FIG. 1A.

FIG. 3C' is a cross sectional view of a valve according to the present invention showing the buttress can straddle the channel;

DETAILED DESCRIPTION (a) First Embodiment of the Invention

Figure 1A:
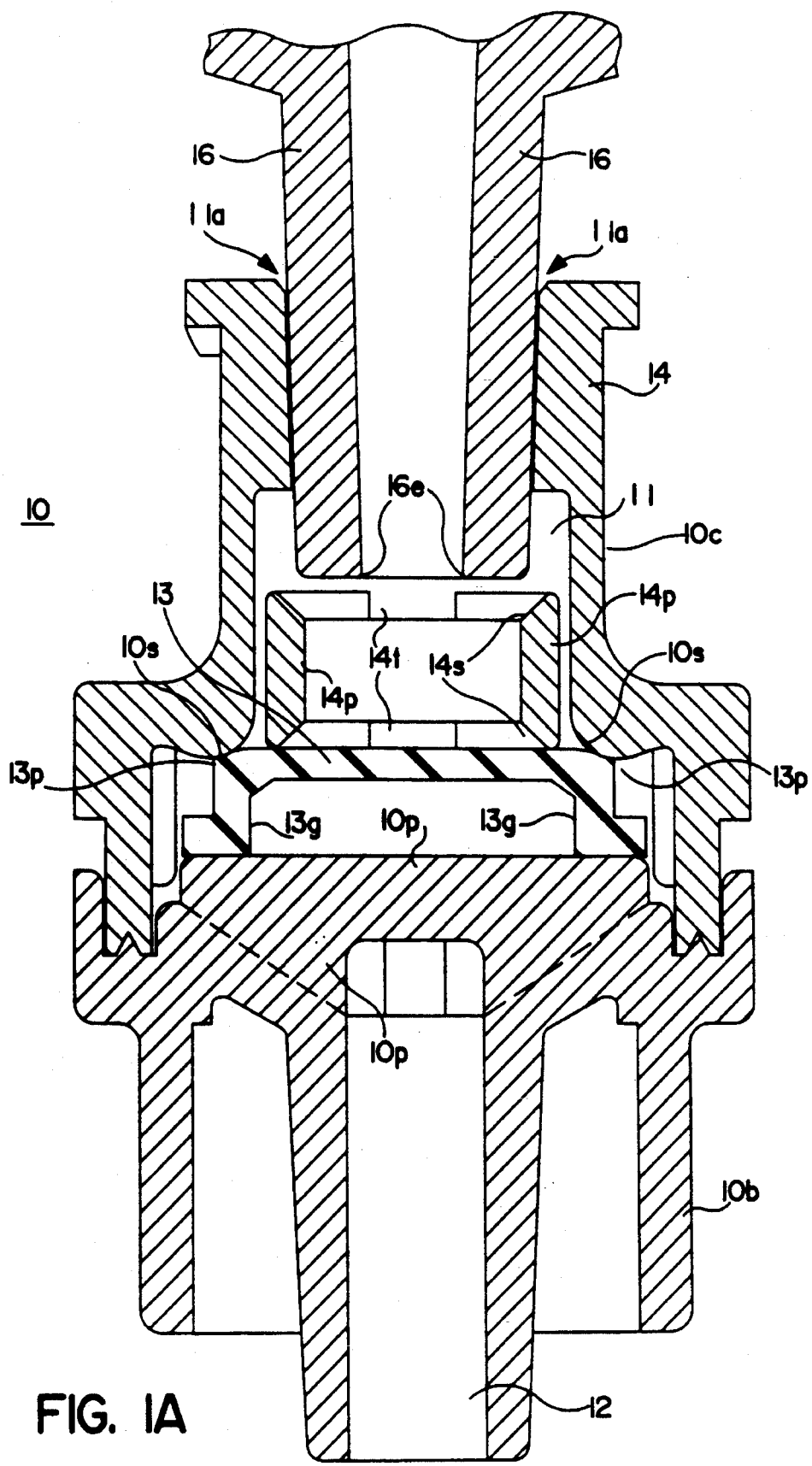
FIG. 1A is a cross-sectional view of a flow-control valve and coupling device in accordance with the invention.

With reference to the drawings, a coupling device 10 in accordance with the invention is shown in FIG. 1A. The device 10 is formed by a base 10b and a cap 10c. The cap 10c contains an aperture 11a for a flow channel 11.

The cap 10c also includes a mount or housing 14 that contains a plunger 14p and receives a flow input fitting, such as a Luer fitting 16. It will be understood that other forms of flow input fitting may be employed as well, such as tubing. Flow from the channel 11 is extended to an output channel 12 in accordance with the operation of a sealing member 13. The sealing member 13 closes the channel 11, preventing upward flow in the channel 12.

In the channel 11, when the plunger 14p is moved downwardly, or there is downward fluid pressure in the housing 14, the sealing member 13 is unseated. In either case, the sealing member 13 is moved away from its seat 10s in the cap 10c as pictured in FIG. 1B. This illustrates the role of the plunger 14p in unsealing the member 13. Conversely, when plunger 14p moves to its upward, original position, the member 13 is reseated. Alternatively when downward pressure is terminated, the member 13 is reseated.

Figure 1C:
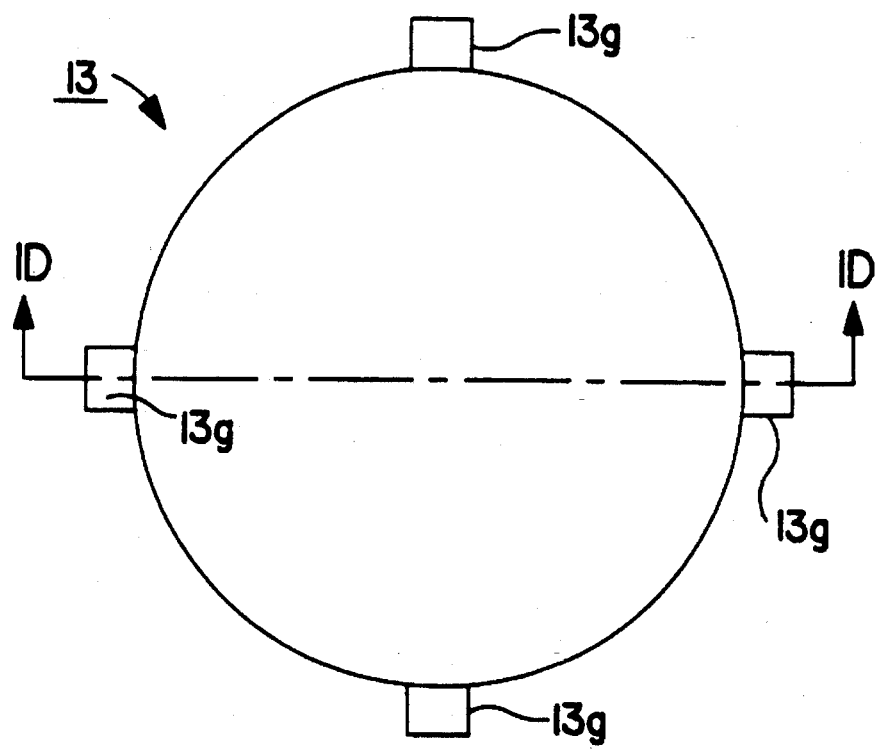
FIG. 1C is a plan view of the sealing member used in the device of FIGS. 1A and 1B before assembly into the device.
Figure 1D:
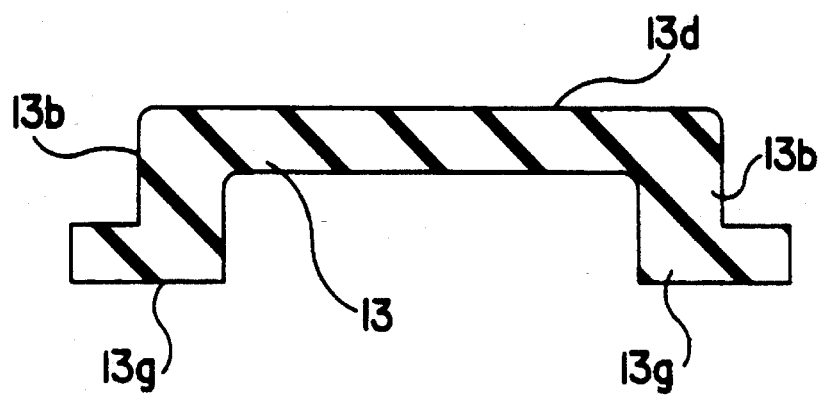
FIG. 1D iS a sectional view of the sealing member of FIG. 1C taken along the lines 1D—1D.

In order to properly seat the member 13 when there is no downward pressure, the base member 10b includes a platform 10p that acts upon legs 13g, which are shown in detail in FIG. 1C and forces the upper periphery 13p of the member 13 against the seat 10s of the cap 10c. This produces a circumferential indentation in the member 13 as indicated in FIG. 1A.

In addition to having the member 13 opened by pressure, the invention provides the internal plunger 14p which can be actuated externally of the device 10, for example by a Luer fitting 16 as shown in FIG. 1B. The end 16e of the Luer fitting engages the end of the plunger 14p, and pushes it downwardly to open the member 13 independently of whether there is downward fluid pressure.

The valve in FIGS. 1A and 1B achieves a number of advantages. The use of a sealing member 13 with peripheral legs 13g assures that the valve 10 will be in its sealed condition after each opening. This avoids the inadvertent shift in position which can take place when a sealing diaphragm is instead used and seated by the action of a central prong.

The particular plunger shown in FIGS. 1A and 1B is in the form of a cylinder with tapered upper and lower lips 14s, which are interrupted by circumferentially positioned, radial slots 14t. The slots 14t facilitate the flow of fluid. The slots 14t are symmetrically disposed on opposite lips of the plunger 14p in order to facilitate manufacture and avoid difficulty in assembly since the symmetry of the plunger makes the direction of insertion irrelevant.

Where the sealing member is in accordance with FIG. 1C, it has four tabs which are diametrically opposed with respect to transverse diameters. The sealing member 13 has a "hat-like" construction and is molded from an elastomer with a hollow dome 13d with a base 13b from which the tabs 13g extend.

(b) Second Embodiment of the Invention

Figure 2A:
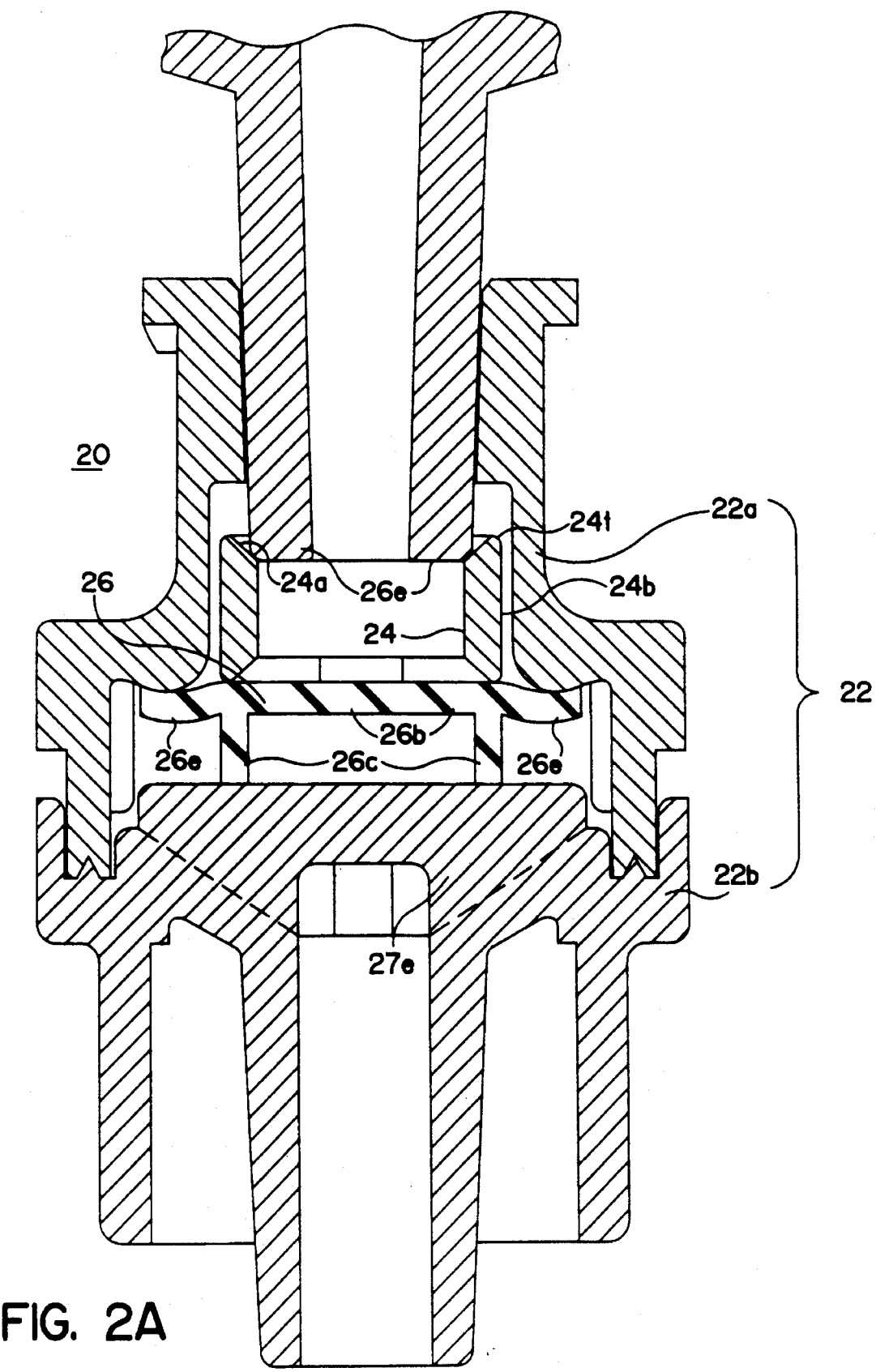
FIG. 2A is a cross-sectional view of an alternative coupling device in accordance with the invention.
Figure 2B:
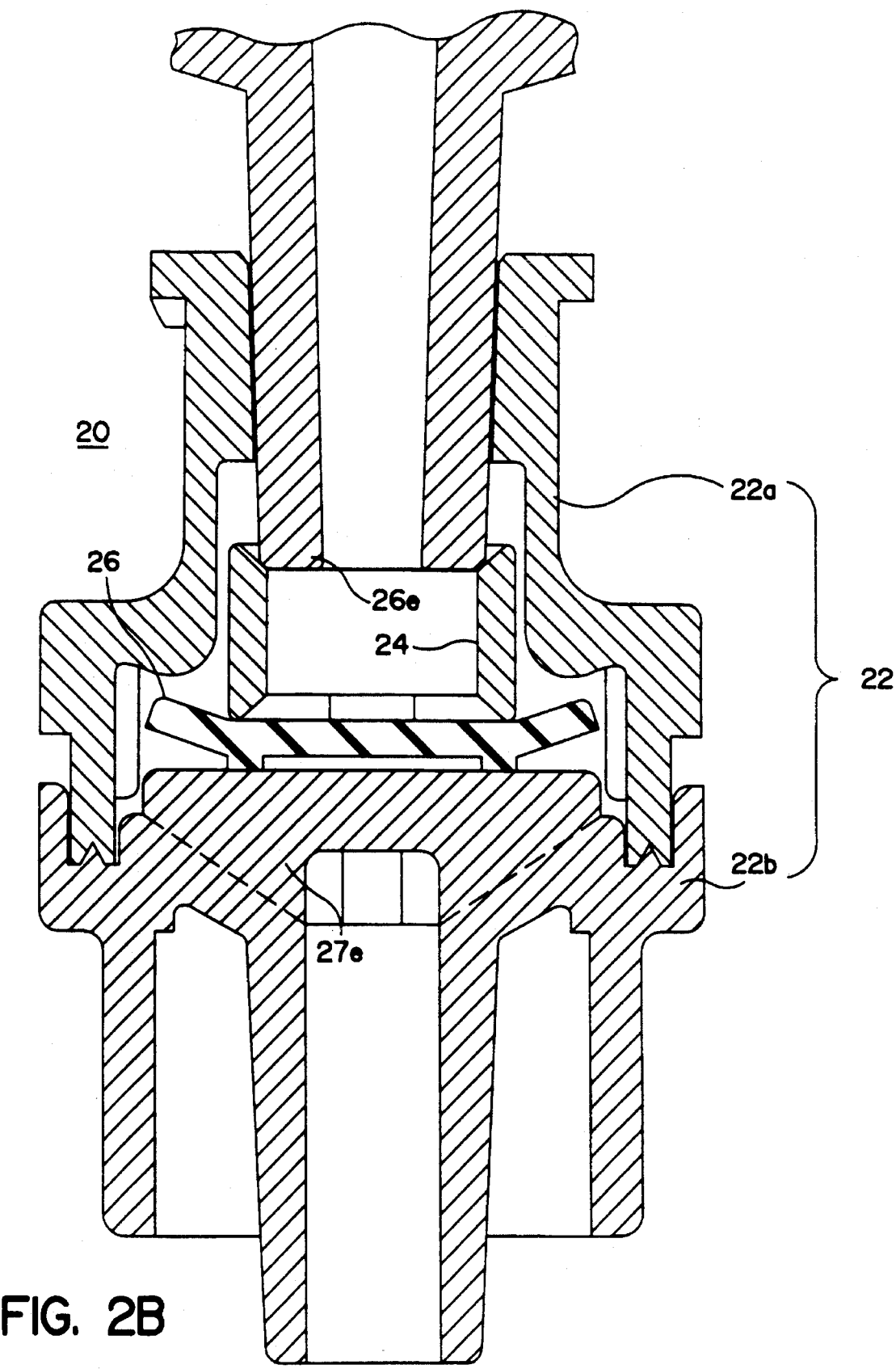
FIG. 2B is a further view of FIG. 2A illustrating the action of an internal plunger against the sealing mechanism of the device in FIG. 2A.
Figure 2C:
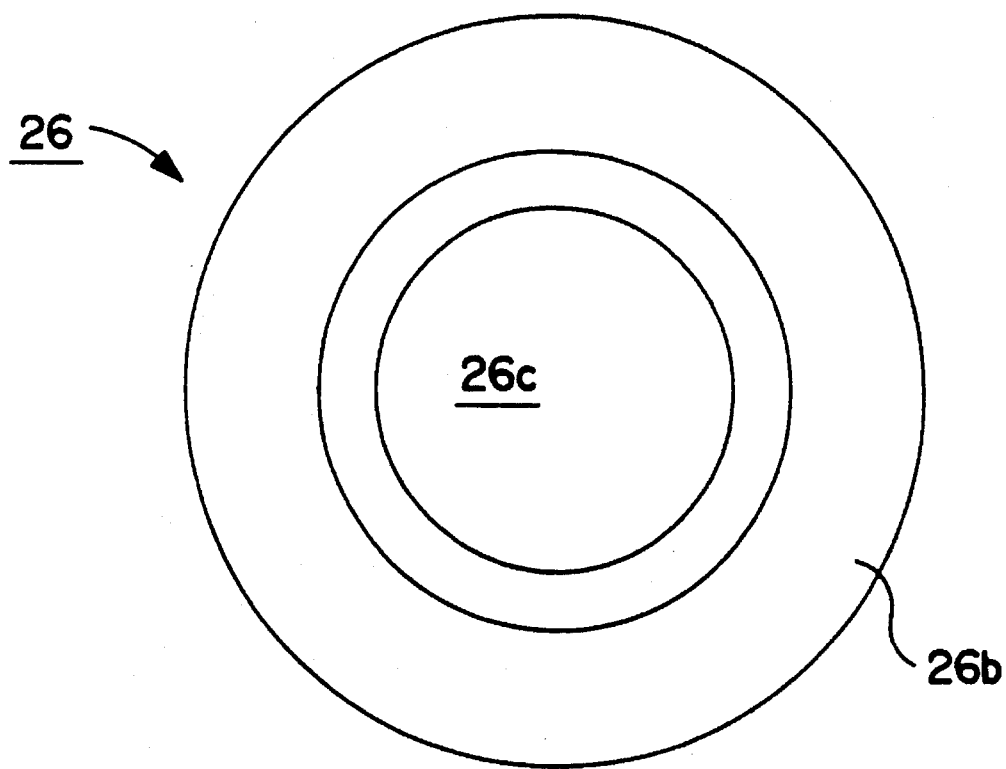
FIG. 2C is a bottom plan view of the sealing member used in the device of FIGS. 2A and 2B before assembly into the device.
Figure 2D:
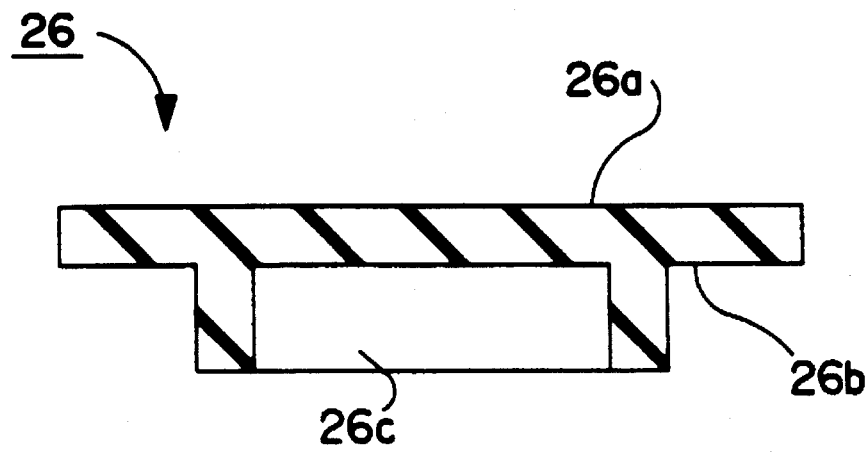
FIG. 2D is a sectional view of the sealing member of FIG. 2C taken along the lines 2D—2D.

An alternative flow control device 20 in accordance with the invention is shown in FIGS. 2A and 2B. In the device 20, there is a housing 22 with two parts 22a and 22b. The part 22a includes a plunger 24 and a flexible disc 26 with a circumferential cup 26c that is coaxial with the body 26b and inwardly displaced from its edges 26e. The plunger 24 serves to permit opening of the disc 26 externally of the device 20, by, for example a Luer fitting of the kind used in FIGS. 1A and 1B. Generally, the device 20, like the device 10 of FIG. 1A, can be used for continuous intravenous fluid administration to a patient, as well as inspiration and aspiration.

When therapy of a patient requires supplemental intravenous medication, or other intermittent fluid administration, the device of FIG. 2A is supplemented, so that a syringe or other injection apparatus can be used to insert medication into the intravenous fluid. This can be accomplished by inserting an injector into a branch channel.

The housing 22 accommodates both the flexible plunger 24 and the valve disk 26. The flexible plunger 24 within the housing 22a is similar to the plunger 14p of FIGS. 1A and 1B. The plunger 24 includes a top 24t, a cylindrical body 24b, and a tapered inlet 24a. The inlet 24a is specially designed to receive the end 26e of the Luer fitting 26 shown in FIGS. 2A and 2B. The use of a flexible coupling 24b is important to assure that the Luer fitting will seal the inlet of the housing 22a, and simultaneously act upon the plunger. In the absence of a flexible plunger, because of tolerance variations, some Luer tips will seal the housing inlet without making contact with the plunger. Because of the flexible coupling, the Luer fitting will make the necessary seal with the housing inlet and simultaneously open the associated disk. In other cases the Luer fitting goes in completely and contacts the plunger, driving it into the disk without sealing the housing inlet. This can jam the disk so that it stays in its open position even after the Luer fitting is removed.

For some cases of a rigid plunger, the disk could be forced away from its seat before making the necessary seal. In other cases the seal could be made before the desired contact with the plunger.

Illustrative details of a Luer coupling are shown with respect to a portion 22b of the Luer device in FIGS. 2A and 2B. The body portion 22b also can have an inner wall (not shown) provided with threads for attachment to a suitable portion of the flow structure.

Structurally the disc 26 has opposed surfaces 26a and 26b, with a cup 26c joined or integrated with the surface 26b.

Buttresses 27e, of which only one buttress is shown in FIGS. 2A and 2B, are affixed to the lower body element 22b. The purpose of the buttresses 27e is to assure engagement with the cup 26c of the disc 26 and force the surface 26a into a sealing position. In addition, the buttresses are spaced apart to assure that there will be adequate passage for liquid flow about the peripheral edge of the disc 26.

The component elements of the device 20 are joined, for example, by ultrasonic welding. Upon assembly the buttresses apply pressure to the disc 26, which is then held in position. The design of the disk 26 assures that any inadvertent side-to-side movement will not interfere with seating.

With respect to the plunger 24 as shown in FIGS. 2A and 2B, the body portion 24a includes a skirt or side wall 24w that is apertured at its top and base, and extends circumferentially. The plunger 24 is approximately cylindrically-shaped with a grooved bottom that engages the disk.

(c) Illustrative Actual Size Valves

Figure 4A:
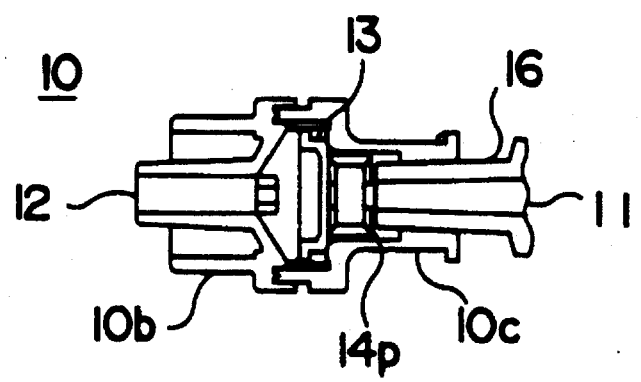
FIGS. 4A and 4B are respective cross-sectional views of illustrative actual size devices in accordance with FIGS. 1A and 3A.
Figure 4B:
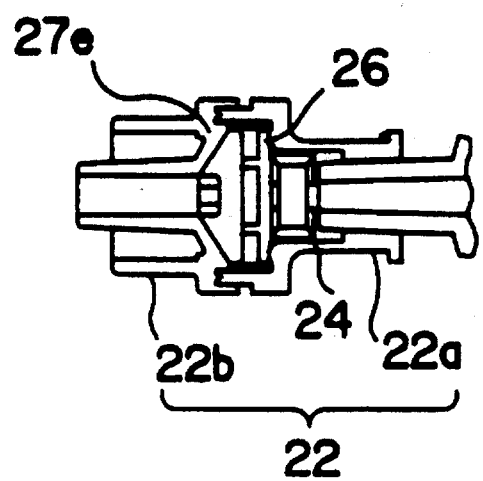

An actual size cross-sectional view of the embodiment of the device 10 is shown in FIG. 4A, while the corresponding cross-sectional view of the device 20 is shown in FIG. 4B.

To complete the structure 10 and 20, a unitary lower part is ultrasonically welded to the upper part. The ultrasonic welds are at the base of a trough which extends completely around the upper portion of one part. Because the devices 10 and 20 are formed by two-part housings, assembly of the device is relatively simple. The assembly is readily accomplished by inserting the plunger and the sealing member into the cap of one member. The second member is then seated against the first member, and the ultrasonic welding accomplished. The structure of the sealing members assures positive seating. In addition, the base includes buttresses or ledges which limit the extent to which the diaphragm is opened by pressure in the inlet sleeve. Once the sealing member is opened, the inlet flow is guided to the outlet.

(d) Third Embodiment of the Invention

Figure 3A:
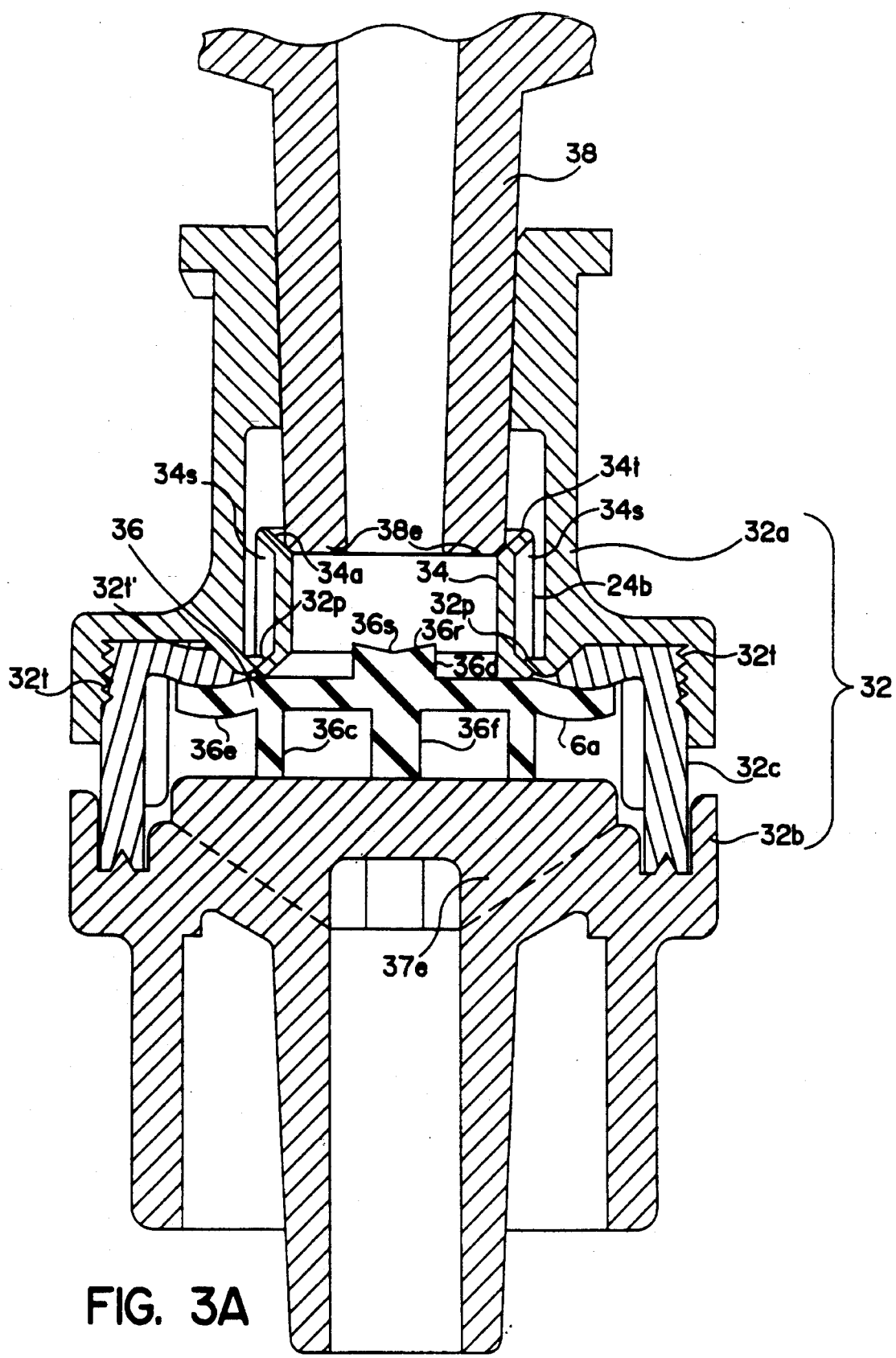
FIG. 3A is a cross-sectional view of an alternative embodiment of the invention for use with a cannula.
Figure 3B:
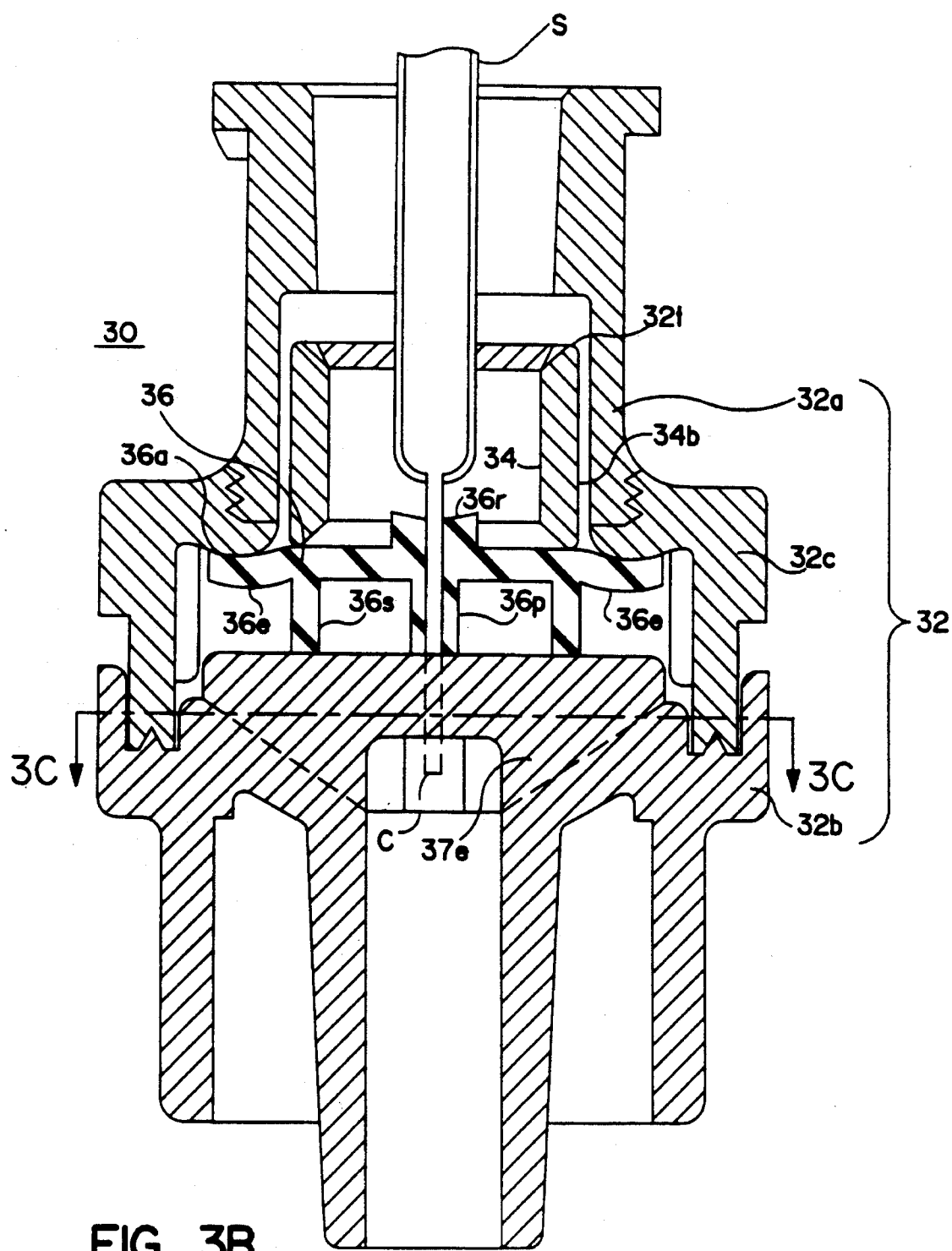
FIGS. 3B and 3C are views of a modification of FIG. 3A showing an inserted cannula in FIG. 3B, and in cross-section in FIG. 3C along the lines 3C—3C of FIG. 3B.

An alternative flow control device 30 in accordance with the invention is shown in FIGS. 3A and 3B. In the device 30, there is a housing 32 with three parts 32a, 32b and 32c. The part 32a includes a plunger 34, while the part 32c includes a flexible disc 36 with a circumferential cup 36c that is coaxial with the body 36b and inwardly displaced from its edges 36e. The plunger 34 serves to permit opening of the disc 36 externally of the device 30, by, for example a Luer fitting of the kind used in FIGS. 1A and 1B. Generally, the device 30, like the device 10 of FIG. 1A, can be used for continuous intravenous fluid administration to a patient. In addition the part 32a can be separated from the part 32c. For that purpose the parts 32a and 32c have mating screw threads 32t. To promote the fit of the parts 32a and 32C, there is a taper 32t' between them.

When therapy of a patient requires supplemental intravenous medication, or other intermittent fluid administration, the device of FIG. 3A can be supplemented to permit a syringe, or other injection apparatus, to be used to insert medication. This can be accomplished by using an injector with a branch channel.

In addition the device 30 permits the insertion of a syringe S, which can have a blunt end as shown in FIG. 3B, or a pointed end. The disk 36 includes a ridge 36r to provide a depression that acts as a guide for a needle or cannula. The disk 36 also includes a post 36p with a slit 36s. The ridge 36r has an edge 36d to limit the extent to which prior fluid may enter the depression at the slit 36s. In addition the post 36p has sufficient thickness to keep the domed member 36 from becoming unsealed at the edges 36e when the cannula is being used. At the same time the post 36p is sufficiently flexible to permit cannula entry as shown in FIG. 3B.

The housing 32a–32c accommodates both the flexible plunger 34 and the valve disk 36. The flexible plunger 34 within the part 32a is similar to the plunger 14p of FIGS. 1A and 1B, except that in FIG. 3A it is held within the part 32a when the latter is removed from the part 32c. The plunger 34 includes a top 34t, a cylindrical body 34b, and an apertured inlet 34a. The inlet 34a is specially designed to receive the end 36e of the Luer fitting 38 shown in FIG. 3A, while a blunt cannula C is shown inserted in FIG. 3B. The use of a flexible coupling 34 is important to assure that the Luer fitting 38 will seal the inlet and simultaneously act upon the plunger 34. In the absence of a flexible plunger 34, because of tolerance variations, some Luer tips will seal the inlet without making contact with the plunger 34. Because of the flexible coupling, the Luer fitting will make the necessary seal with the inlet and simultaneously open the associated disk 36. By contrast for some cases of a rigid plunger, the disk 36 could be forced away from its seat before making the necessary seal. In other cases the seal could be made before the desired contact with the plunger.

Structurally the disk 36 (FIG. 3B) has opposed surfaces 36e and 36b, with a cup 36c joined or integrated with the surface 36b.

Buttresses 37e, of which only one buttress is shown in FIGS. 3A and 3B, are affixed to the lower body element 32b. The purpose of the buttresses 37e is to assure engagement with the cup 36c of the disk 36 and force the surface 36a into a sealing position. In addition, the buttresses are spaced apart to assure that there will be adequate passage for liquid flow about the peripheral edge of the disk 36.

Figure 3C:
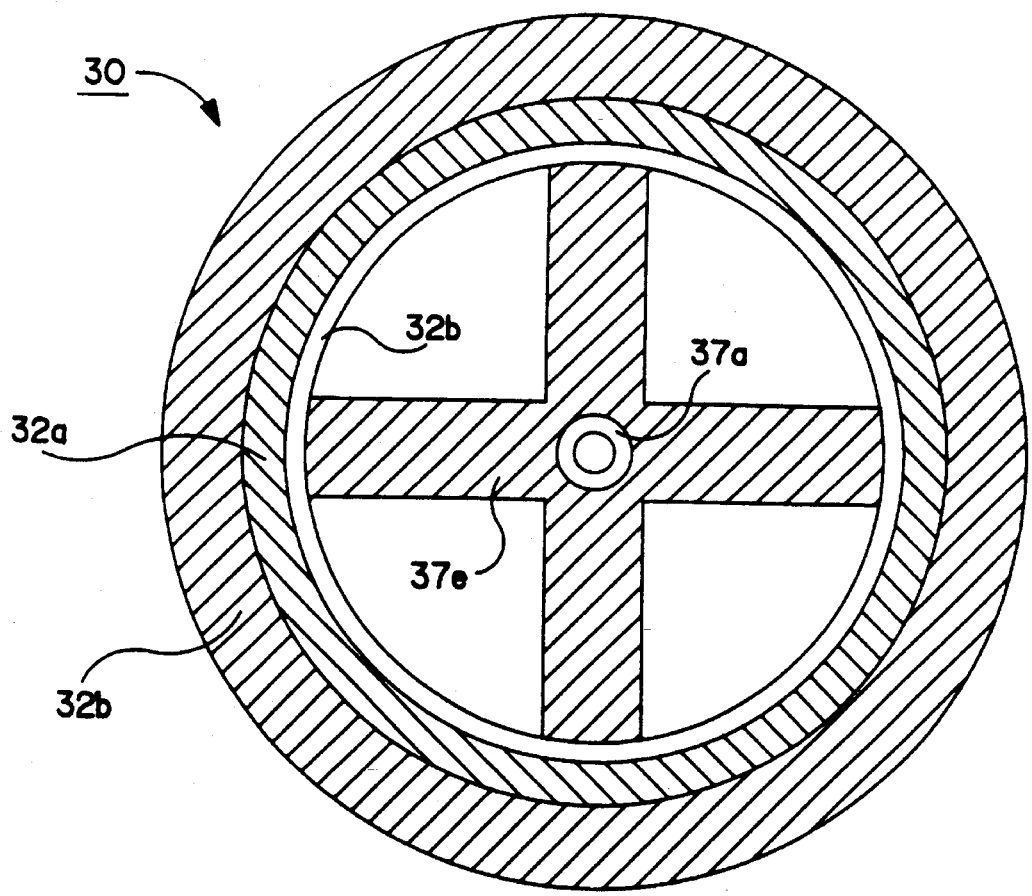
Figure 3C:
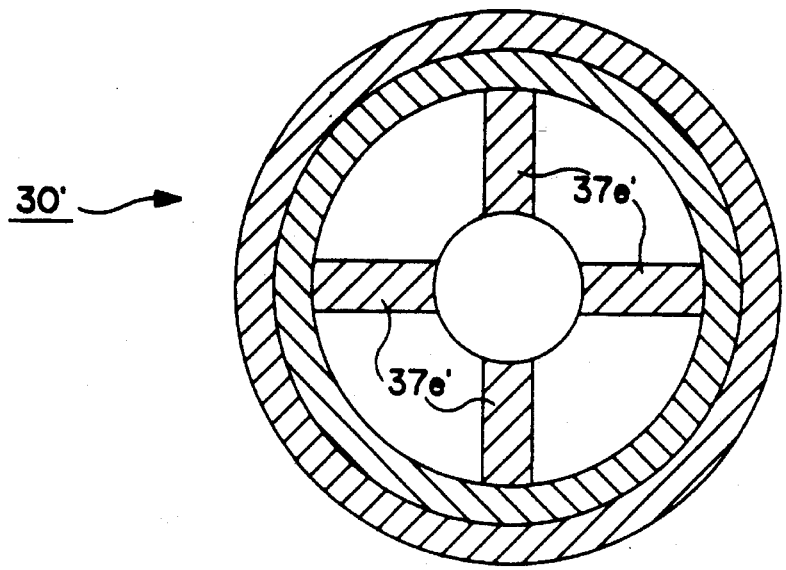

It will be understood that the buttress 37e of FIG. 3B can straddle the channel to increase the size of the flow path as shown in FIG. 3C' for the buttresses 37e'.

The elements 32b and 32c of the device 30 are joined, for example, by ultrasonic welding. Upon assembly the buttresses 37e apply pressure to the disk 36, which is then held in position. The design of the disk 36 assures that any inadvertent side-to-side movement will not interfere with seating.

As shown in FIG. 3B, insertion of a blunt cannula C of a syringe S produces momentary separation of the slit 36s and allows the tip of the cannula to enter the flow channel of the device.

In order to permit movement of the cannula tip through the buttress 37e, the latter has an aperture 37a as shown in FIG. 3C which is a cross-section of FIG. 3B taken along the lines 3C—3C.

Figure 3D:
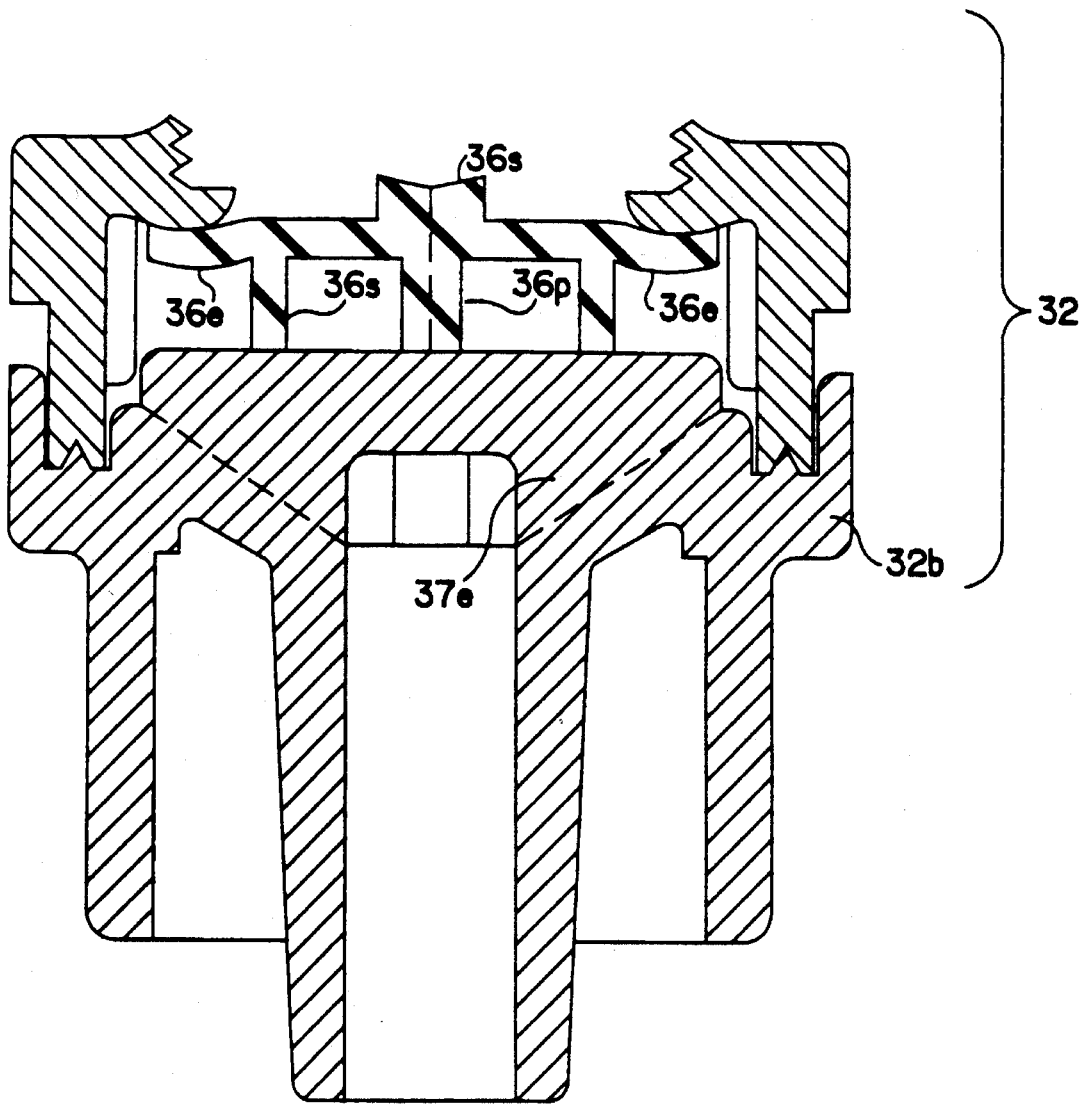
FIG. 3D is a view of FIG. 3B with the top portion removed to provide direct access to the domed member of FIG. 3A.
Figure 3E:
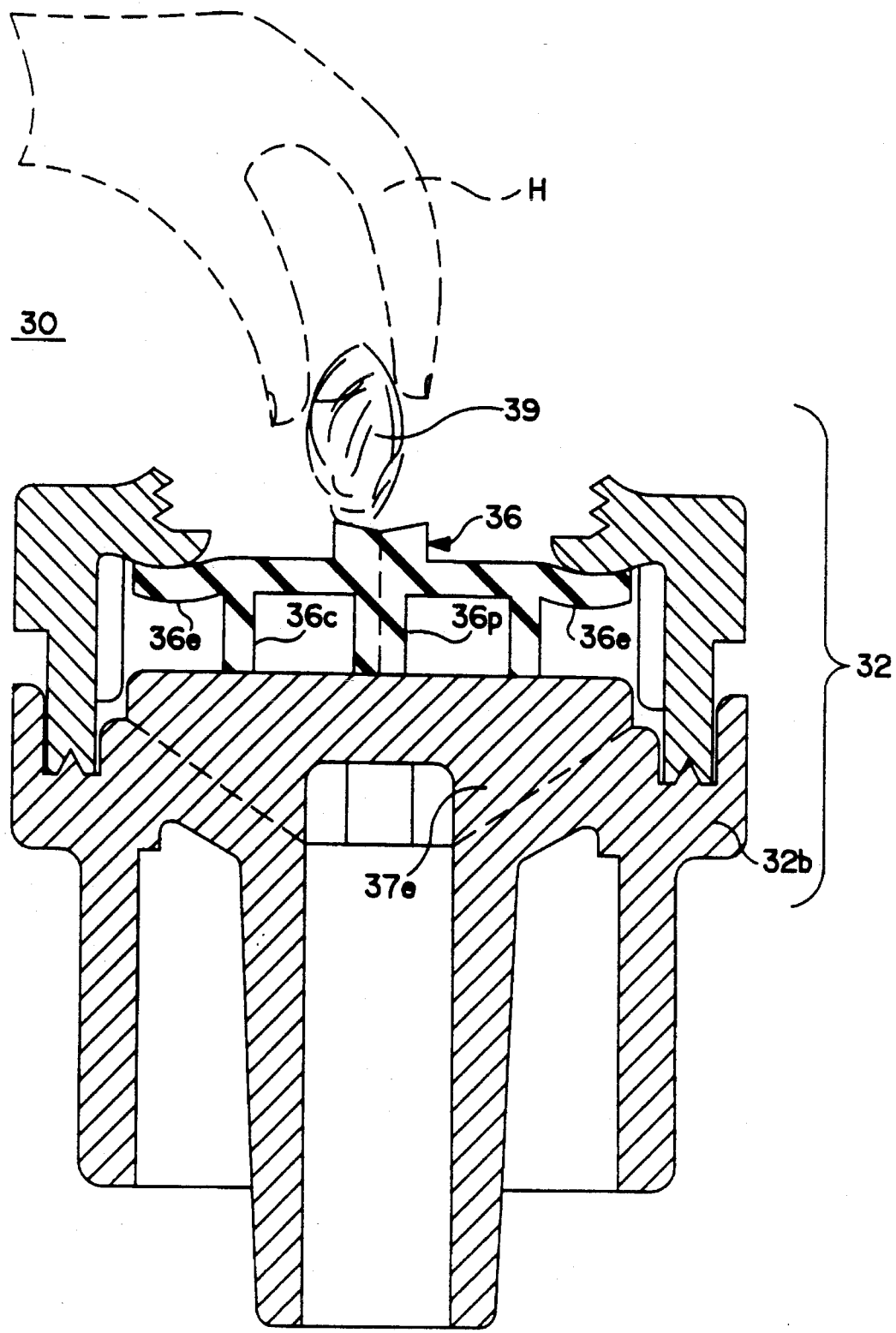
FIG. 3E is a view of FIG. 3D illustrating swabbing for sterilization of the domed member of FIG. 3B prior to cannula or needle insertion.

In addition, to promote sterility the upper portion 32a is removed from the central portion 32c, with the result shown in FIG. 3D. This provides direct access to the disk 36. In FIG. 3E there is an illustration of using a swab 39 for sterilization of the domed member 36 of FIG. 3B prior to cannula insertion. The phantom hand H holding the swab 39 is not to scale in relation to the valve 30.

(e) Further Embodiment of the Invention

Figure 5:
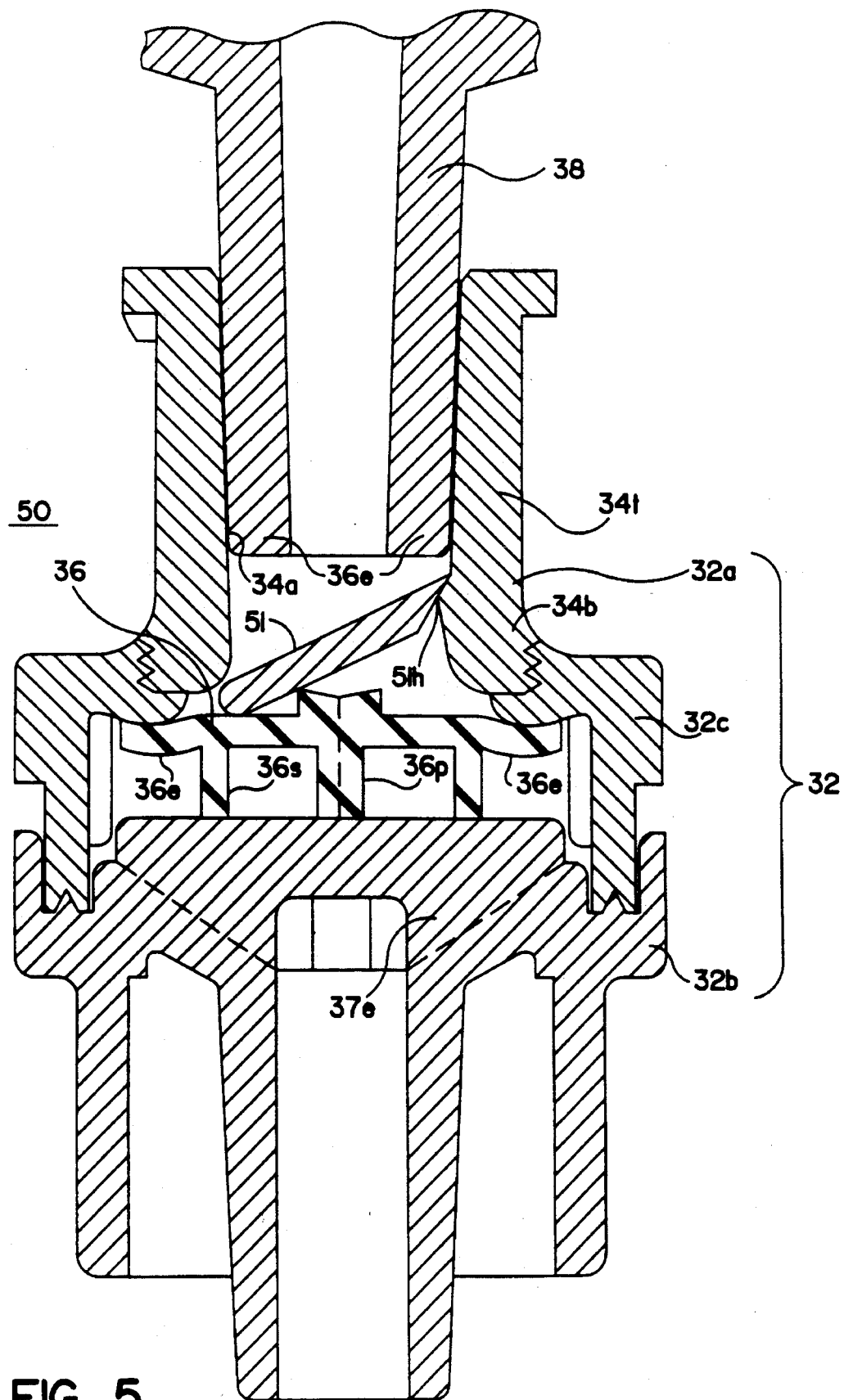
FIG. 5 is a further alternative embodiment of the invention for Luer activation of a modification of the device of FIG. 3B.

In the further embodiment 50 of FIG. 5, the plunger 34 of FIGS. 3A and 3B has been removed and replaced by a lever plunger 51 that is hinged at position 51h, and can be in contact with the disk 36 near a sealing position in relation to the part 32c. When the fitting 38 is pushed downwardly, it pushes the lever 51 against the disk 36, compressing the adjacent portion of the cup 36c and unsealing the nearby edge 36e of the disk 36. The hinge at position 51h facilitates the downward leverage of the lever 51 when the fitting 38 is pushed downwardly. In the particular embodiment of FIG. 5 the tip of the lever 51 is opposite the cup 36c.

In addition, presence of the lever 51 can prevent the insertion of a cannula or needle until the part 32a is separated from the part 32c. Consequently, the disk 36 must be exposed for antiseptic swabbing before cannula or needle insertion can take place. Another advantage of the lever arrangement of FIG. 5 is that the lever 51 remains in position when the part 32a is separated from the part 32c.

I will be understood that the foregoing detailed description is illustrative only, and that other aspects and modifications of the invention will be apparent to those of ordinary skill in the art without departing from the scope of the invention as defined by the appended claims.

What is claimed is:

1. A flow control device comprising (a) a housing with internal walls defining a channel with a step change from a first diameter to a second, larger diameter for the flow of fluid, providing a valve seat at said step change, and providing a buttress in said channel axially spaced from said valve seat;

(b) a resilient valve element in the shape of a disk of a diameter greater than said first diameter and less than said second diameter with an annular extension extending axially from one face and the opposite face being essentially flat, said valve element situated in said channel with said flat face seated against said valve seat and said annular extension pressed against said buttress for controlling flow therethrough; and (c) a plunger reciprocatingly situated within the first diameter portion of said channel for engaging and applying pressure to unseat said valve element from said valve seat.

2. Apparatus as defined in claim 1 wherein said plunger is in the form of a cylinder with axial slots.

3. Apparatus as defined in claim 1 wherein said resilient valve element includes a slit in the central portion thereof for accommodating a cannula.

4. Apparatus as defined in claim 3 wherein said slit is surrounded by a depression in the essentially flat face of said resilient valve element to guide said cannula into said slit.

5. Apparatus as defined in claim 4 wherein said slit is surrounded by a post extending from the central portion of the annular extension face of said resilient valve element to prevent said cannula from depressing said resilient valve element.

6. A flow control device in accordance with claim 1 further comprising means for providing direct access to the essentially flat face of said resilient valve element to permit the sterilization thereof.

7. Apparatus as defined in claim 6 wherein said means for providing sterilization access comprises means for attaching and detaching a detachable portion of said housing defining a portion of the first diameter portion of said channel at a point proximal to said valve seat.

8. Apparatus as defined in claim 7 wherein said detachable housing portion further comprises means for preventing insertion of a needle or cannula into the essentially flat face of said resilient valve element when said detachable housing portion is attached.

9. Apparatus as defined in claim 8 wherein said prevention means comprises a hinged lever.

10. Apparatus as defined in claim 1 wherein said plunger is made of resilient material.

11. Apparatus as defined in claim 1 wherein said plunger is a cylinder internally beveled at the end distal from said valve element.

* * * * *